March 9, 1965 W. E. SILVA Plant Pat. 2,486
APPLE TREE
Filed Oct. 30, 1963
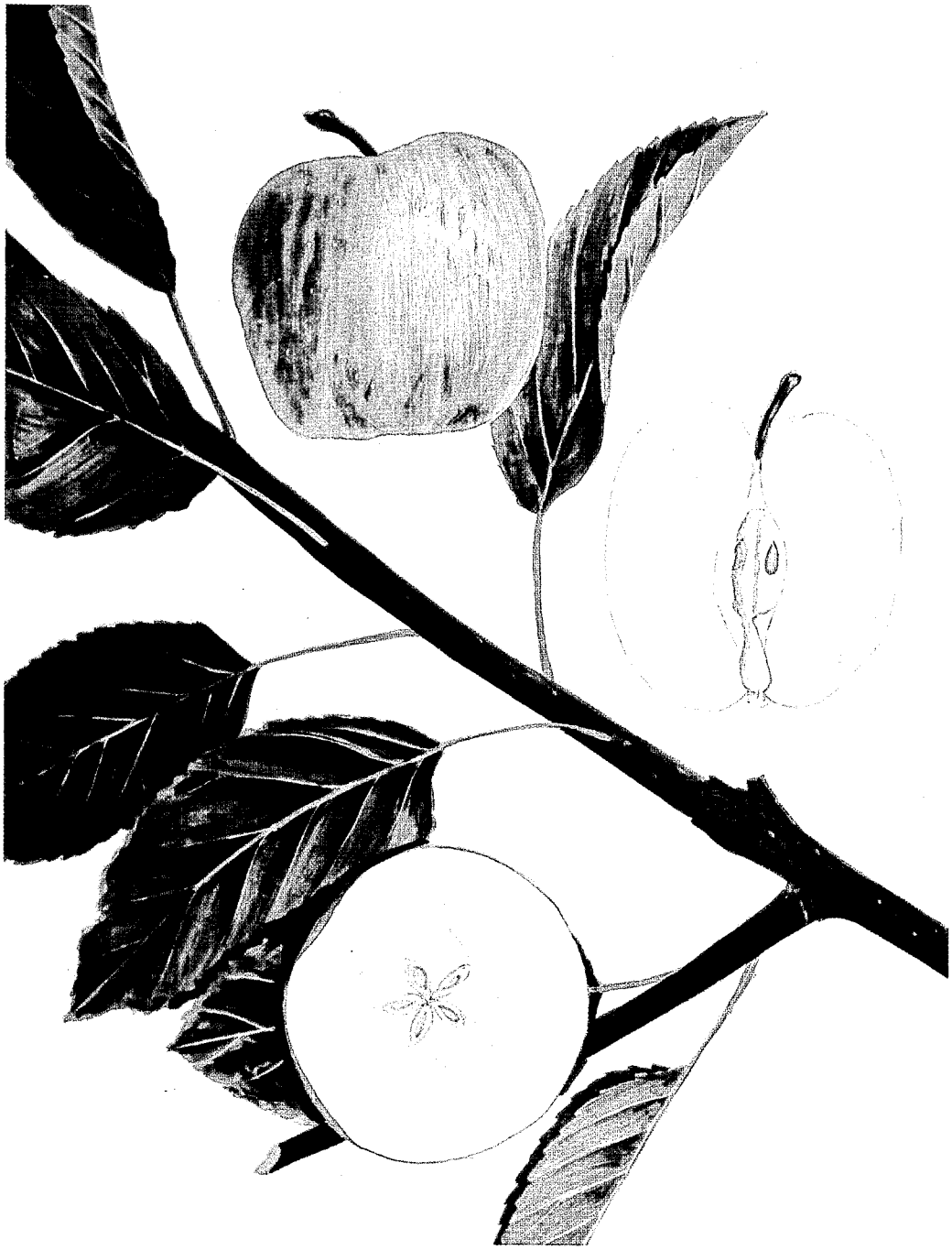
WITNESS
Samuel H. Shrop
INVENTOR
WILLIAM E. SILVA
by Rummler & Snow
ATTYS.

United States Patent Office

Plant Pat. 2,486
Patented Mar. 9, 1965

2,486
APPLE TREE
William E. Silva, 408 Water Trough Road,
Sebastopol, Calif.
Filed Oct. 30, 1963, Ser. No. 320,244
1 Claim. (Cl. Plt.—34)

My present invention concerns a new and distinct variety of apple tree which was developed by me as the result of planned breeding efforts carried on since 1945 at my breeding grounds at Sebastopol, California. My primary objective was to produce a red apple having a high percentage of total solids and which would have improved storage and keeping qualities as well as good flavor, minimum shrinkage when baked in a pie, and good canning qualities.

My new variety of apple tree was originated as a seedling developed by cross breeding Red Delicious × Red Rome Beauty, as the pollen parent, with Gravenstein as the seed parent, all of these varieties being unpatented. The new variety of apple tree appears to have obtained the objectives and advantages which I was seeking, and which will be further discussed herein, and I have asexually propagated the new variety, by grafting, through several generations at Sebastopol, California, to find the novel characteristics of the plant to be fixed and to hold true.

My new variety of apple tree is a heavy producer of fruit with fruiting spurs occurring so profusely as to require considerable thinning. Generally, each fruiting spur produces three apples and these have long stems, a relatively small core, and a very thin skin of a mottled red color and having a dark red overtone with a yellow undercoat. The flesh is solid, crunchy when eaten uncooked, of fine flavor, and will not rot during storage or become soft and corky in the spring.

The fruit of my new apple tree has excellent keeping qualities, keeping all winter in California in the open and without shrinkage. It appears to keep longer in bins and stores than any of parent varieties, it does not shrink or disintegrate in pies, it has a very strong pleasant aroma when cooked, and it has a pronounced pleasing sub-acid flavor rather than the bland flavor found in many other varieties.

The fruit ripens during the month of October, in California, and has great persistence in hanging onto the tree instead of falling as apples so often do. This results in a high percentage harvest of fully ripened fruit for commercial use. Also, the ripened fruit has an extraordinarily high sugar content and repeated tests, from season to season, show an average of substantially 23.4 to 23.75 percent total solids and sugar.

The accompanying drawing in full color, shows typical examples of the fruit and foliage of my new apple tree, the views showing the fruit in both axial and transverse cross section as well as in elevation; and the following is a more detailed description of the new variety with color designations according to Maerz and Paul's "A Dictionary of Color."

*The tree*

Origin: Seedling.
*Seed parent.*—Gravenstein (unpatented).
*Pollen parent.*—Red Delicious × Red Rome Beauty (both unpatented).
Classification: Hybrid.
Growth habit: Vigorous.
Height: Approximately 20 feet.
Trunk: Heavy and smooth.

Branches: Substantially perpendicular to trunk; spreading and dense with smooth bark and profuse production of fruiting spurs. Color—Plate 8, C–11.
Foliage: Heavy.
*Leaves.*—Abundant, 2 to 3¾ inches long and up to about 2 inches wide. Stem—1¼ inches long. Shape—ovate with serrate margins. Texture—smooth. Pubescence—none. Color: upper side—green, Plate 22, L–2 to L–6; under side—green, Plate 21, F–4. Petiole—1½ to 1¾ inches long, no pubescence; color—Plate 21, L–1 with red tone Plate 5, L–6.
*Twigs.*—Long and strong. Fruit spurs 1¼ inches apart. 15 lenticels to a fruit spur.
Disease resistance: Appears to resist scab, mildew and blight present in the area where grown.

*Flowers*

Blooms: Early, about April 10 in California. Blossoms are about ⅝ inch diameter, with 5 rose red petals. Very short anthers of a light green color and with light yellow pollen. Filaments 1/12 inch long, light green color. Pistils, syncarpous—with 5 stigmas, light green color.

*The fruit*

Shape: Height and diameter about equal, wider adjacent the base and tapering toward the calyx end.
Size: 2½–2¾ inches high. 2½–2¾ inches transverse diameter.
Color: Mottled. Generally red—Plate 4, L–4 to L–6 with yellow undercoat—Plate 11, L–3 and a dark red overtone—Plate 6, L–5 to L–6.
Stem: About ¾ to 1 inch long and 1/16 to 3/32 inch in diameter.
*Color.*—Plate 13, C–12.
*Cavity.*—⅝ to 1 inch diameter, ⅜ inch deep.
Basin: ¾ to ⅞ inch diameter, ¼ inch deep.
*Calyx.*—Closed; segments small and convenient.
*Eye.*—⅛ to ¼ inch diameter.
*Tubes.*—5/16 to 7/16 inch deep, ⅛ to ¼ inch wide.
*Color.*—Green, Plate 17, J–5.
Core:
*Seed cavity.*—1 inch long, ½ inch wide.
*Seeds.*—¼ to 5/16 inch long, ⅛ inch wide.
*Color.*—Brown, Plate 13, F–11.
Skin: Very thin and smooth. No wax. Scarfskin—wanting. Bloom—wanting.
Flesh: Juicy, with firm texture, crunchy when eaten.
*Flavor.*—Sub-acid, very tasty.
*Aroma.*—Heavy and pleasing.
*Total solids and sugar content.*—23.4 to 23.75%.
*Color.*—Yellow, Plate 9, C–1.
Maturity season: October.
Keeping quality: Very good—keeps all winter in open storage in California. Needs no refrigeration. Does not shrink during storage.
Use: Very good eating apple. Excellent for pies and canning. Does not mush or disintegrate when baked in pies.

In general my new variety of apple is particularly distinguished by its very high content of total solids and sugar, its crispy and firm flesh, the ability to bake in pies without shrinking or disintegration of chunks, and its very good keeping qualities under open storage conditions; and by the heavy production of fruit on the mature tree which fruit tends to hang onto the tree long after full ripening.

Having described my new variety of apple tree, I claim:

A new and distinct variety of apple tree, substantially as shown and described, particularly characterized as to novelty by the very high percentage of total solids and sugar in its fruit, the ability of the fruit to keep well in open storage without refrigeration and its good cooking qualities, the high fruit production characteristic of the tree, and the persistence of the fruit to stay on the tree after ripening.

No references cited.

ABRAHAM G. STONE, *Primary Examiner.*